United States Patent [19]

Greff

[11] Patent Number: 5,891,428
[45] Date of Patent: Apr. 6, 1999

[54] PHYSICALLY ACTIVE ANTIMICROBIAL GEL FOR COSMETIC PRODUCTS

[75] Inventor: Daniel Greff, Mere, France

[73] Assignee: Sederma S.A., Le Perray-en-Yveline, France

[21] Appl. No.: 11,057

[22] PCT Filed: Aug. 2, 1996

[86] PCT No.: PCT/FR96/01229

§ 371 Date: Feb. 4, 1998

§ 102(e) Date: Feb. 4, 1998

[87] PCT Pub. No.: WO97/05856

PCT Pub. Date: Feb. 20, 1997

[30] Foreign Application Priority Data

Aug. 4, 1995 [FR] France .................................. 95 09512

[51] Int. Cl.$^6$ .................................................. A61K 31/74
[52] U.S. Cl. .................... 424/78.03; 424/78.08; 424/78.31; 424/78.37; 424/405; 514/844; 514/944

[58] Field of Search ............................... 424/78.03, 78.31, 424/78.37, 405, 78.08; 514/844, 944

[56] References Cited

U.S. PATENT DOCUMENTS 5,437,867 8/1995 Vichroski et al. ....................... 424/401
5,686,088 11/1997 Mitra et al. ............................. 424/404

*Primary Examiner*—Jose' G. Dees
*Assistant Examiner*—Michael A. Williamson
*Attorney, Agent, or Firm*—Young & Thompson

[57] ABSTRACT

A gel, in a proportion of 1 to 20% of the finished product, contains at least one polyol, one (meth)acrylic acid polymer and one fluidification solvent of general formula (1): $R_1-O-(R_2-O-R_2)_n-OR_3$, wherein $R_1$ is a hydrogen atom or a straight or branched C1–C5 alkyl chain, $R_2$ is a straight or branched C1–C5 alkyl chain, $R_3$ is a hydrogen atom or a straight or branched C1–C5 alkyl chain, and n is an integer of 1 to 200,000.

10 Claims, No Drawings

PHYSICALLY ACTIVE ANTIMICROBIAL GEL FOR COSMETIC PRODUCTS

FIELD OF THE INVENTION

The invention pertains to a physically active antimicrobial gel for cosmetic or dermatopharmaceutical products.

BACKGROUND OF THE INVENTION

Most cosmetic or dermatopharmaceutical products designed for topical application—whatever the galenic form: H/E, E/H emulsion, milk, lotion, gel, solution—contain one or more microbicidal substances in their formulation. The reasons for this are obvious: the raw materials used for the manufacture of these products are only rarely perfectly sterile, the finished products are too fragile (perfume, biologically active compounds, vitamins) to uphold sterilization following conditioning. It is thus necessary to protect the product from any microbial contamination which could be detrimental to the health of the user or to the aesthetic appearance of the product. This contamination can arise from the manufacturing process (including the raw materials used), from a packaging that is not hermetically sealed and above all following opening, from the environment or the user himself.

In contrast to food products or to pharmaceutical products, cosmetic products are not required to exhibit an expiration date; they can and must therefore be stable and in perfect condition—including microbiologically—for a long time.

The chemical preservatives used in these products fulfil this protective role. The choice of antimicrobial substances or biocidal molecules being used is strictly controlled by the different legislation of European, American and Asian countries.

Since to be effective all preservative must be chemically active, destroying either the cellular wall or the biochemical mechanisms of microbial cells, it is not surprising that these same biocidal molecules sometimes have a detrimental effect on the human cells with which they come into contact. It is a fact that with the increased use of cosmetic or dermatopharmaceutical products, a parallel increase in cases of intolerance (irritation, allergy) to these products has been observed. The studies performed by various dermatologists, pharmacists or health authorities reveal that a number of these incidents can be attributed to the preservatives contained in the products.

Moreover, the ecological trend of our time reinforces the desire of the cosmetic industry to offer "natural", "mild" or "hypoallergenic" products. Means of protecting the creams without the incorporation of preservatives are been sought.

The formulation of cosmetic products without preservatives is however not easy. It is presently possible, using selected, sterile raw materials and ensuring manufacture under strict aseptic hygiene conditions (conditioning under laminar flow into sterile containers). Remains the risk of contamination during use. Only the choice of a specific packaging, designed to deliver the dose for use at the time of application, and preventing any entry of air and germs inside the container, can satisfy these constraints.

As a result, the diversity of the ranges of cosmetic products that can be prepared without preservative is limited, and above all the cost of manufacture and conditioning is significantly increased.

Patent FR 2 682 296 proposed a non-chemical method of preservation that is based on the use of gels of the glyceryl poly(meth)acrylate type, the property of which is to exert a strong osmotic effect on its environment, making it possible to inactivate the microorganisms introduced into the cosmetic preparation through water deprivation. Microbiological tests of overcontamination (for example, the inoculation of $10^6$ germs/gram of a cream containing 40% of the gel in question is controlled in 7 days only when the gel is present in the formulation, in the absence of any chemical preservative) have been able to demonstrate this antimicrobial efficacy of the gel. The method described in this patent has proven applicable in practice, but it has a number of disadvantages: the amount of gel required in a cosmetic formulation is very high (minimum 40% in the best cases; often the gel must be incorporated at the rate of 30%, even 60%). This limits the field of application, as the formulator is subjected to constraints in his freedom to adapt the texture, the touch of the products. Another disadvantage came out of successive testing: protection of the finished products to contamination by particular moulds (ex: *Aspergillus niger*) is very difficult to achieve, this germ requiring very little free water for its growth; it is therefore less sensitive to the water deprivation brought about by the gel.

SUMMARY OF THE INVENTION

One aim of the invention is to propose a gel with an increased efficacy in preserving cosmetic products, particularly against the moulds that are likely to grow, that is to say a gel with improved osmotic properties.

Another aim of the invention is to propose a gel with improved cosmetic characteristics, especially the touch.

Yet another aim of the invention is to propose a gel that is physically active and with an antimicrobial efficacy, which can be incorporated into the formulation of the cosmetic product, in a proportion less than or equal to 20% Unless otherwise indicated, all percentages refer to weight percentages.

DETAILED DESCRIPTION OF THE INVENTION

The object of the present invention is a physically active antimicrobial gel for cosmetic or dermatopharmaceutical products, containing at least one polyol and at least one polymer of (meth)acrylic acid, characterized in that it contains in addition at least one fluidification solvent of general Formula

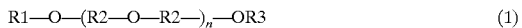
$$R1\text{—}O\text{—}(R2\text{—}O\text{—}R2\text{—})_n\text{—}OR3 \tag{1}$$

wherein R1 is a hydrogen atom or a straight or branched C1–C5 alkyl chain, R2 is a straight or branched C1–C5 alkyl chain, R3 is a hydrogen atom or a straight or branched C1–C5 alkyl chain, and n is an integer of 1 to 200.000, and in that the proportion of gel in the finished product is of approximately 1% to approximately 20%.

According to other characteristics:

each of the polyols is of general formula

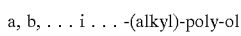
a, b, . . . i . . . -(alkyl)-poly-ol wherein:
- alkyl is a straight or branched Cn alkyl chain, with n ranging from 2 to 10,
- poly is the number of alcohol functions,
- a, b, . . . i, represent different numbers from 1 to 10, corresponding to the substitution positions of the alcohol functions;

in preference, R1 is a C1–C3 alkyl chain and n has value 1 to 3.

the proportion of fluidification solvents in the gel is of 5 to 50% and preferentially from 15 to 30%;

the polymers are derived from acrylic and/or methacrylic acid and are in the form of salts, esters, amides of these acids;

the proportion of polymers in the gel is of 0.05 to 5% and preferentially from 0.2% to 1%;

the proportion of polyols in the gel is of 1 to 99% and preferentially from 30 to 70%;

the polyols are made up of glycerin in the proportion of 30 to 50% and of 1,2-octane-diol in the proportion of 2 to 8%.

the proportion of gel in the finished product is preferably from 5 to 20%.

The invention also has for object the application of the aforementioned gel to the preservation of cosmetic or dermatopharmaceutical products in view of its physical antimicrobial activity.

The invention is described below by means of non-limiting examples for the various components of the gel which is itself made up of polyols, of polymers of the poly(meth)acrylate type, of fluidification solvents and of water.

The polyols, the general formula of which is

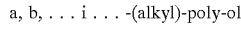

may be, by way of example:

propyleneglycol (a=1, b=2, n=3)
1,3 butyleneglycol (a=1, b=2, n=4)
glycerin (a=1, b=2, c=3, n=3)
1,2 pentane diol (a=1, b=2, n=5)
1,2 octane diol (a=1, b=2, n=8)
1,8 octane diol (a=1, b=8, n=8)
mannitol or sorbitol (a=1, b=2, c=3, d=4, e=5, f=6, n=6)
2 ethyl-1,3-hexane diol (a=1, b=3, n=8, branched).

The polyols are preferably chosen as mixture with a high proportion of glycerin. A particularly preferred mixture contains glycerin in a proportion in the gel of 30 to 50%, and 1,2 octane diol in a proportion in the gel of 2 to 8%.

This mixing of another polyol with glycerin improves the touch, the formulation and increases the osmotic effect of the gel, that is to say its ability to capture free water, hence its antimocrobial efficacy.

The polymers are preferably chosen among the sodium, potassium, triethylamine, triethanolamine, ammonium salts of acrylic and/or methacrylic acid, but also among the esters or amides of these acid polymers, or the crosslinked derivatives of the cobomer type—crosslinkage through allyl ethers of pentaerythritol, sucrose, or propylene for example.

The proportion of polymer in the gel is of 0.05 to 5% and preferably from 0.2 to 1%.

The fluidification solvents are preferably chosen among ethers such as methoxydiglycol, ethoxydiglycol (or diethyleneglycol monoethylether), propoxydiglycol, butoxydiglycol, diethyleneglycol monopropylether, or esters thereof such as ethoxydiglycol acetate, or ethoxyethanol acetate, for example. Fluidification solvents may also be chosen among polyethyleneglycols or polypropyleneglycols, the degree of polymerisation of which possibly reaching 200,000. These solvents are advantageously used as mixtures.

An example of gel according to the invention is made up of:

40% glycerin and 6% 1,2-octane diol,
0.7% sodium polyacrylate,
20% ethoxydiglycol.

The remainder, or 33.3%, is comprised of water.

The gel according to the invention is incorporated into the finished product in a proportion possibly varying from 1 to 99% but, preferably, from 5 to 20%.

The gel according to the invention may be used in any galenic form used in cosmetics requiring antimicrobial preservation: H/E and E/H emulsions, milks, lotions, gels, ointments, hair lotions, shampoos, conditioners, soaps, this list not being limitative.

The gels of the invention can be combined in cosmetic compositions with any other ingredient usually used in cosmetics: lipids of extraction and or of synthesis, gelling polymers and polymers used to increase viscosity, surfactants and emulsifiers, hydro- or liposoluble active principles, plant extracts, tissue extracts, marine extracts.

The cosmetic compositions containing the gels of the invention may be aimed at the treatment or care of the skin, hair, nails and scalp, that is to say anti-ageing treatment, anti-wrinkles, anti-inflammatory, the treatment of acne, sun and free-radical protection, hydration and smoothing effect, treatment against the fall of the hair, its protection against pollution and aggression.

It is particularly interesting to use the gels of the invention in cosmetics and dermatopharmaceutical products made for sensitive, easily irritated skins, hence to incorporate them into so-called "hypoallergenic" or "soothing" products, for example: they have an anti-irritant property.

The efficacy of these gels is based on a physical effect (osmose). It permits the formulation of finished products which are free of chemical preservatives.

I claim:

1. Physically active antimicrobial gel for cosmetic or dermatopharmaceutical products, containing at least one polyol, at least one polymer of (meth)acrylic acid, and a fluidification solvent wherein the fluidification solvent is of general formula $$R1-O-(R2-O-R2)_n-OR3 \tag{1}$$

wherein R1 is a hydrogen atom or a straight or branched C1–C5 alkyl chain, R2 is a straight or branched C1–C5 alkyl chain, R3 is a hydrogen atom or a straight or branched C1–C5 alkyl chain, and n is an integer of 1 to 200,000, and in that one of the polyols is glycerin, and wherein the proportion of polyols in the gel is from 1 to 99% by weight; the proportion of polymers in the gel is from 0.05 to 5% by weight; the proportion of fluidification solvent in the gel is from 5 to 50% by weight; and the proportion of glycerin is from 30 to 50% by weight.

2. Gel according to claim 1, wherein each of the polyols is of general formula

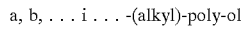

wherein:

alkyl is a straight or branched Cn alkyl chain, with n ranging from 2 to 10, poly is the number of alcohol functions, a, b, . . . i, represent different numbers from 1 to 10, corresponding to the substitute positions of the alcohol functions.

3. Gel according to claim 1, wherein R1 is a C1–C3 alkyl chain and n has value 1 to 3.

4. Gel according to claim 1, wherein the proportion of fluidification solvent in the gel is from 15 to 30% by weight.

5. Gel according to claim 1, wherein the polymers are derived from acrylic and/or methacrylic acid and are in the form of salts, esters, amides of these acids.

6. Gel according to claim 1, wherein the proportion of polymers in the gel is from 0.2 to 1% by weight.

7. Gel according to claim 1, wherein the proportion of polyols in the gel is from 30 to 70% by weight.

8. Gel according to claim 6, wherein the polyols are made up of 1,2-octane-dyol in the proportion of 2 to 8% by weight.

9. Cosmetic or dermatopharmaceutical preparation containing a gel according to claim 1 in a proportion of 5 to 20% by weight.

10. Application of the gel according to claim 1 to the preservation of cosmetic or dermatopharmaceutical products in view of its physical antimicrobial activity.

* * * * *